United States Patent [19]

Smith et al.

[11] Patent Number: 5,801,059
[45] Date of Patent: Sep. 1, 1998

[54] METHOD FOR DETECTING TOTAL KETONE BODIES IN URINE

[75] Inventors: Jack V. Smith, St. Petersburg; Jesse M. Carter, Tampa, both of Fla.

[73] Assignee: Chimera Research & Chemical, Inc., Largo, Fla.

[21] Appl. No.: 616,479

[22] Filed: Mar. 19, 1996

Related U.S. Application Data

[60] Division of Ser. No. 429,292, Apr. 24, 1995, Pat. No. 5,516,700, which is a continuation-in-part of Ser. No. 68,956, May 28, 1993, abandoned.

[51] Int. Cl.$^6$ .................................................. G01N 33/493
[52] U.S. Cl. ........................... 436/128; 436/164; 436/48
[58] Field of Search ............................. 436/128, 904, 436/164, 43, 48, 49

[56] References Cited

U.S. PATENT DOCUMENTS 5,326,697  7/1994  Magers ........................ 436/128
5,510,245  4/1996  Magers ........................... 436/63

*Primary Examiner*—Lyle A. Alexander
*Attorney, Agent, or Firm*—Larson & Larson, P.A.; Herbert W. Larson

[57] ABSTRACT

Aliquot of a urine sample is placed in a first automated analyzer sampling cup and a known standard is placed in a second cup. The urine sample and standard are transferred to separate cuvettes and at least one reagent composition in an aqueous medium is injected into the cuvette. The reagent composition contains a compound to remove substances in the urine interfering with a calorimetric reaction, a compound to convert B-hydroxybutyric acid in the urine to acetoacetic acid in the presence of nicotinamide adenine dinucleotide and reading at a specified wavelength to determine quantitatively the total ketone bodies in the patient's urine.

8 Claims, No Drawings

METHOD FOR DETECTING TOTAL KETONE BODIES IN URINE

PRIOR APPLICATIONS

This application is a divisional of application Ser. No. 08/429,292, filed Apr. 24, 1995, now U.S. Pat. No. 5,516,700 which is a continuation-in-part of application Ser. No. 08/068,956, filed May 28, 1993, (now abandoned).

BACKGROUND OF THE INVENTION

This invention relates to a method and materials that are designed for use in automating urinalysis. This system is designed to analyze urine for its constituents by a method that is fully automated (does not require the use of manual methods such as refractometer, pH meter, dipsticks, or impregnated test strips). Automation as designed by this system is directed to the use of a self-operating instrument that is capable of handling multiple reagents designed for use on an automated analyzer system for the quantitative determination of total ketone bodies in urine.

It is known that the most common method for the analysis of urine is by the use of a manual technique known as a dipstick. This method for the analysis of urine is labor, time intensive, and costly among other detriments. The use of a dipstick for analysis of urine also relies on the subjective interpretation of the technician. The dipstick method requires the technician to submerge the dipstick in a sample of urine and remove it, wait a specified time, then compare the color development of the test on the dipstick to a color chart. Even more cumbersome methods involve the use of a refractometer, pH meter, or manual chemistry test.

The following list of assay devices utilizing prior art includes dry tablets, dipsticks, or impregnated test strips for the analysis of urinary constituents. None of the prior devices foresee or teach a multiple or single liquid reagent system designed specifically for auto-analyzers to analyze urinary constituents quantitatively.

One such U.S. Pat. No. 4,147,514 discloses test strips (dipsticks) for the detection of ketone bodies. The assay strips are made up of a chemical bonded to a cellulose pad on a strip. This is then dipped into a specimen sample. This method only determines ketone bodies qualitatively at its best, due to inability of the system to allow the use of standards and controls on the same strip to which the sample is applied.

Another such patent, U.S. Pat. No. 3,146,070 discloses analytical compositions in dry form on a bibulous carrier (dipstick) impregnated with a pH indicator for the determination of pH. This assay at best only determines pH qualitatively, due to the inability to use standards and controls located on the same strip for the same test sample to define and verify a quantitative determination.

Additionally, U.S. Pat. No. 4,318,709 discloses a device comprising a carrier matrix (dipstick) impregnated with the test means for specific gravity. This assay at best only determines specific gravity qualitatively, due to the inability to use standards and controls located on the same strip for the same test specimen. The prior art in this case also did not foresee the wide specimen to specimen matrix variations of real world urine samples including matrix components such as pH, and ionic strength, and the concomitant requirement of a multiple reagent system to effectively analyze urine for specific gravity in a liquid to liquid reaction. The normal pH value for urine can range from 4.5 to 8.0, which if using the prior dipstick method the results would be widely scattered and inaccurate without a reagent component to neutralize this effect prior to completion of the assay.

Various devices are described in the literature for the determination of particular urinary constituents one by one with the use of carrier matrices (dipstick, microcapsule, filter paper, etc.). None of the prior art teaches or elucidates a means for determining by automated technology urinary constituents from a single sample of urine, via multiple tests that are reported simultaneously by an autoanalyzer using liquid reagents specifically designed for this family of instruments. As cited by the prior art, (in package insert literature) when evaluating laboratory test results, definitive diagnostic, or therapeutic decisions should not be based on any single result or method. However, the prior art states that dipsticks are affected by high specific gravity and substances that cause abnormal urine color such as phenyl ketone, or phthalein compounds and thus may affect the readability of the urinalysis reagent strips (dipsticks). In addition, sulfhydryl-containing compounds such as mercaptoethane sulfonate sodium, and levadopa metabolites may cause false positive results or atypical color reactions using the prior art.

SUMMARY OF THE INVENTION

The automated urinalysis system of this invention offers a method for reducing the consumable materials and labor costs. The system also offers increased accuracy, sensitivity, and objective quantifiable determinations of urinary constituents for better diagnostic interpretation of the test results of urine, thus enabling a physician to provide better health care for the patient.

This invention satisfied many of the problems unanswered by the prior art: quantitative results, non-subjective results, reproducible results, increased accuracy, precision, sensitivity, carrier free reagents, reagents designed for autoanalyzer use, reagents uniquely designed for each particular urine analyte assay overcoming matrix problems previously unanswered by prior art, a method allowing vast improvement of test completion time (hundreds to thousands per hour). The present invention presents a fully automateable walk-away urinalysis system applicable to any discrete autoanalyzer currently in use, and obviously represents a marked advancement in the art of urinalysis. The clear cut object of the present invention is to provide a more comprehensive method for determining urinary constituents of total ketone bodies, such method specifically yielding improved health care.

Thus, it is a primary objective of the present invention to provide techniques for determination of urinary constituents of total ketone bodies at low chemically significant levels.

An additional object of this invention is to make available an advanced method for analyzing a sample of urine for the quantitation of its constituents on an autoanalyzer. The advanced ability of the automated urinalysis system to offer a means for automated analysis on urine is a significant improvement in the art of urinalysis.

Additionally, the object of this invention is to provide a comprehensive method which is broadly adaptable to a wide variety of automated analyzers presently in use in the industry which will increase accuracy, sensitivity, precision, and speed. An autoanalyzer allows for precise quantitative results beyond the scope and abilities of the prior art. An autoanalyzer, used in conjunction with the automated urinalysis reagents described herein, provides a system that produces an objective quantitative result of an unknown urine sample obtained from a linear standard curve determined by analysis of standards run on the instrument, and verified as accurate by quantifying controls of known value. This simultaneous analysis of standards, controls, and unknowns (urine samples) yielding unbiased results improves the art of urinalysis significantly over the prior art, which yields only qualitative and subjective results.

It is a further object of this invention to provide a method for the simultaneous determination of multiple urinary components including total ketone bodies from a single urine sample using a system of reagents designed for autoanalyzer use. This improvement in the science of urinalysis over the prior art proves to be significant medically and economically.

Another object of this invention is to provide a method that yields quantifiable results in the determination of urinary constituents present in a sample of urine.

Yet another object of this invention is to provide uniquely formulated reagents for each urinalysis assay that were not taught or envisioned by the prior art, and overcome the inadequacies of the prior art. Consider the fact that one of the primary means of optimizing enzymic assays is identifying the best temperature, and performing the assay at that temperature. The prior art can only be used at room temperature which can vary over a wide range from test location to location, and from day to day in the same facility. Such variation adds to the imprecision, insensitivity, and inaccuracy of the prior art. Conversely, the present invention is compatible with current autoanalyzers which precisely control temperature of the reaction cuvettes as prescribed by the assay parameters. Thus, this invention's enzyme-based and nonenzyme-based assays can be optimized for temperature thereby obtaining consistent results with even greater sensitivity, precision, and accuracy then previously possible.

Yet another very important object of this invention is to provide uniquely formulated reagents for this assay that were not taught or envisioned by the previous art, and in doing so provide a previously unavailable aid to medical diagnosis of patient health. It is known that analysis of ketone bodies can serve as a useful tool in evaluation of the metabolic status of patients suffering from diabetes. In this regard a very useful tool is the ratio of acetoacetic acid to B-hydroxybutyric acid. This ratio is of particular interest because it shifts dramatically if the treatment regime is successful. This ratio can only be determined using this instant invention, but not the prior art.

Still another object of this invention is to provide a method for the determination of objective results (from the photometric analysis by the automated analyzer) instead of the subjective determination (from human observation). The present invention provides a unique formulated reagent system that can be mixed with unknown urine samples, standards, and controls and then be read spectrophotometrically with unbiased accuracy on an autoanalyzer. The use of the automated urinalysis system provides a means for improved accuracy, precision, and specificity by removal of the subjective human element from the analysis. Clearly, a system that automatically dispenses, measures, and records results is a marked improvement in the science of urinalysis.

Yet another object of this invention is to provide uniquely formulated reagents for each urinalysis assay that were not taught or envisioned by the prior art, and overcome the inadequacies of the prior art. Consider the fact that urea is the largest component or urine (besides water) by a factor of 50% over the next largest component (sodium chloride). A unique chemical formulation to compensate for urea is an advancement in the art of urinalysis. The present invention is a liquid reagent that is not carrier dependent, designed for autoanalysis, and has agents added to remove the urea and other interfering ions from the solution, thus preventing it from interacting with the color developer. These improvements increase sensitivity, accuracy, and precision, thereby allowing the total ketone bodies assay in urine to be quantifiable.

Another object of this invention is to provide uniquely formulated reagents for each automated urinalysis assay that was not taught or envisioned by the prior art. The assay for ketone bodies in the prior art has limited accuracy and application because it is a carrier dependent assay and it only produces semi-qualitative results with its sensitivity ranging from 5 to 10 mg/dl acetoacetic acid to produce a positive result. The prior method produces multiple color changes (at least 3 different colors) for determination of ketone bodies making accurate, precise, and monochromatic spectrophotometric autoanalysis impossible. Some one skilled in the prior art could not easily and effectively convert it to a liquid matrix, as required for use on an autoanalyzer. The prior art is qualitative and only measures acetoacetic acid which constitutes approximately 20% of the total ketone bodies in urine whereas B-hydroxybutyric acid makes up approximately 80% of the ketone bodies in urine. The prior art is susceptible to interferences from sample matrices including, but not limited to, highly pigmented urines, low pH values, high specific gravity and sulfhydryl groups including 2-mercaptoethane sulfonate sodium which causes false positive results and/or atypical color development. The prior art also requires a 40 second incubation period for test completion increasing the chance of operator error, and cost of testing. The present invention is a liquid reagent that is not carrier dependent, and is specifically designed for use on autoanalyzers. The present invention is quantitatively linear from 0.0 to 25 mg/dl of acetoacetic acid or greater in increments of 0.1 mg/dl. The present invention also measures quantitatively the amount of B-hydroxybutyric acid present with a sensitivity range of 0.0 mg/dl to 100 mg/dl B-hydroxybutyric acid. This is done by the use of a colorimetric reagent specifically designed for autoanalyzer use that is sensitive to the presence of acetoacetic acid and B-hydroxybutyric acid in solution. The present invention has a compensator for highly buffered urines and diverse urinary pH which can range from a pH of 4.5 to 8.0 in random urines. The prior art did not teach of or elucidate a method to neutralize the pH and ionic content of a urine prior to assaying acetoacetic acid content. This failure of the prior art to compensate for abnormal pH and buffering directly contributes to its poor accuracy and precision. This lack of precision and accuracy of the prior art is also directly attributable to its lack of sensitivity to B-hydroxybutyric acid, the major component of ketone bodies present in urine. The present invention has curve stabilizers and agents added to compensate for the wide variety of interfering substances found in urine, which the prior art did not teach or envision. Because the present invention measures the presence of B-hydroxybutyric acid which accounts for 80% of the ketone bodies present in urine versus the prior art's sensitivity to acetoacetic acid only, the sensitivity of the present invention is increased by 400%. The present invention can also identify 99% of the ketone bodies present in some of its permutations. The present invention is quantitative, carrier independent, precise, accurate, and sensitive and represents an obvious advancement in the art of urinalysis.

DETAILED DESCRIPTION OF THE INVENTION

The presently claimed method comprises a group of carrier-free liquid reagents designed for simultaneous usage on automated analyzers for quantitative determination of urinary constituents. The automated urinalysis system of the instant invention solves the problems confronting automating the analysis of urine, and in the process, represents a significant improvement over the present art. These improvements which facilitate application to automation and represent significant technical improvement over the previous art include, a buffering system for pH variation in urine by correcting pH to the analytically preferred value prior to analysis and also stabilizing reaction rates thereby improving linearity and neutralizing the interference effects of the highly complex matrix of random urines submitted for analysis. Additional technical improvement is due to the addition of components to remove interfering substances yielding reduced assay limitations and increased linearity, accuracy and precision in the resulting quantitations. These three icons of analysis (linearity, accuracy, precision) are further enhanced by the instant invention's adaptability to autoanalyzers because of the inherent ability of said analyzers to control reaction temperatures. This temperature control allows the use of optimal reaction temperature. These unique reagent formulations allow automation resulting in, but not limited to, enhanced speed, objectivity, accuracy and sensitivity associated with the automated test. A synopsis of the automated testing process follows. The entire automated urinalysis reagent system is loaded into an autoanalyzer. The controls, standards and unknown urine samples are fed into the autoanalyzer, individually mixed with each test reagent in discrete cuvettes, the absorbance read and quantitation determined by comparison with the standard curve.

The composition of each reagent of the present invention is designed for optimum reaction with the random urine samples and to effectively deal with problems arising from the tremendous variability from sample to sample due to the diet, disease state, medications, time of collection, state of hydration, sex, age and physical well being of the patient. All of these factors can interfere with the prior art test procedures.

The automated urinalysis system reagents are individually designed for optimum analysis of specific urinary components. The reagent system for total ketone bodies in urine is carrier independent and has specific agents added to compensate for interference from enzyme inhibitors, highly pigmented urines, sulfhydryl groups, atypical color development, mesna (2-mercaptoethane sulfonic acid), high ion levels (specific gravity), abnormal pH and other normal urinary constituents. The reagent system is composed of a two part reagent (but may consist of a one part reagent). The first reagent (R1) is specifically designed to neutralize matrix interference and increase sample-reagent compatibility with the autoanalyzer. The component, 2,3-butanedione monoxime, can be included in this first reagent (R1) to remove urea and other substances found in urine that cause interference with the calorimetric reaction. Ethylenediaminetetraacetic acid and dimercaptopropanol, are other components of the R1 that can be utilized to neutralize interfering substances by chelation, including compounds that act as enzyme inhibitors and anti-oxidants. These compounds remove oxidizing contaminants such hypochlorite and act as a solution clarifier. Clarifers cause the disappearance of the characteristic yellow color of urine, thereby enhancing spectrophotometric analysis. Bile salts; i.e., choleic acid sodium salt, can be added to enhance solubility, enzyme activity and prevent denaturation of the enzyme. Delta-3 hydroxybutyrate dehydrogenase is added to convert the B-hydroxybutyric acid (which composes 80% of ketone bodies present in urine) to acetoacetic acid. The prior art does not address this 80% fraction of the ketone bodies in urine. Nicotinamide Adenine Dinucleotide (NAD) is also included in the R1. The reaction of Delta-3 hydroxybutyrate dehydrogenase with the B-hydroxybutyric acid in the presence of NAD, results in the reduction of the NAD to B-Nicotinamide Adenine Dinucleotide (B-NADH). This reduction of NAD can be measured spectrophotometrically at 340 nm and corresponds directly to the quantity of the B-hydroxybutyric acid present. If desired, the R1 as heretofore described, can stand as a single reagent for determination of ketone bodies. The total can be extrapolated from the B-hydroxybutyric acid fraction by multiplying its concentration by 1.25 (to compensate for the 20% fraction of total ketone bodies due to acetoacetic acid). The R1 also contains a buffer to adjust sample pH, establish a carrier free matrix and aid in solubility and compatibility of the reagents' complex chemical matrix. This complex chemical matrix requires a complementary aqueous buffering system with unique dynamics capable of adjusting the reaction solution to ideal pKa and promoting reagent solution compatibility with autoanalyzers. Unbuffered solutions have high acidic, or basic activity, or strictly organic properties which are not compatible with autoanalyzer syringes, tubing, metal and plastic parts. The buffer also promotes carrier independence. The R1 also contains surfactants that enhance the reaction, decrease surface tension, promote effective mixing on a molecular level and improve flow dynamics through tubing and syringes of automated analyzers. The R1 also can contain an amino acid to facilitate color formation of the acetoacetic acid with the color developer in the R2. The concentrations of R1 buffers and other components can be varied to compensate for limitations and variations in the configuration of sampling and reagent delivery systems of various makes of available autoanlayzers. The reagent buffers also compensate for abnormal pH of urine samples and urines with high buffer capacities. The total ketone bodies reagent system's second reagent (R2) is the color generating reagent of the two reagent set (unless a single reagent system is used). This second reagent is composed of diazonium salts (e.g., 4-nitrobenzene diazonium tetrafluorborate) which couples with the acetoacetic acid yielding a hydrazo compound that can be monitored at 645 nm. Note, the R1 component, D-3-hydroxybutyrate dehydrogenase converts B-hydroxybutyric acid to acetoacetic acid. Thus, nearly all of the ketone bodies in urine (99%) are in the form of acetoacetic acid. The remaining 1% is acetone. As a result, this method measures 99% of ketone bodies compared to 20% measured by the prior art. Alternatively, the R2 reagent can contain sodium nitroferricyanide which couples with the analyte to form a colored complex measureable at 545 nm. In conjunction with this formulation, the R1 contains an amino acid such as glycine to enable complex formation. The R2 also contains compounds to enhance sodium nitroferricyanide stability and the ensuing color development. These enhancers include (but are not limited to) alkali earth compound metals; i.e., phosphoric acid trimorpholide (in an alkaline buffer), yttrium (in an alkaline buffer), amine (or amine alcohols) and ethylenediaminetetraacetic acid. The reagent is buffered according to which group, or single component is used in the color developing reaction. The R2 also contains a buffer to adjust sample pH and aid in solubility and compatibility of the reagent's complex chemical matrix. This complex chemical matrix requires a complementary, aqueous buffering system with unique dynamics capable of adjusting the reaction solution to the ideal pKa and promoting reagent solution compatibility with autoanalyzers. Unbuffered solutions may have high acidic or basic activity, or strictly organic properties which are not compatible with autoanalyzer components including syringes, tubing and metal and plastic parts. The buffer also promotes carrier independence. The R2 also contains surfactants that enhance the carrier-free matrix, decrease surface tension, promote effective mixing on a molecular level and improve flow dynamics through tubing and syringes of automated analyzers. The concentration and combination of components of the R1 and/or the R2 reagents can be varied to compensate for limitations and variations in the configuration of sampling and reagent delivery systems of various makes of available autoanalyzers. Without further elaboration, it is believed that one skilled in the art can, using the preceding description, utilize the present invention to its fullest extent. The following preferred specific embodiments are, therefore, to be construed as merely illustrative and not limited to the remainder of the disclosure in any way whatsoever. In the following examples, all instrument parameters, reagent combinations and method techniques are set forth.

EXAMPLE 1

The automated total ketone bodies urinalysis reagent system's first reagent (R1) contains surfactant, 2,3-butanedione monoxime, ethylenediaminetetraacetic acid (sodium salt), dimercaptopropanol, bile salts, Delta-3-hydroxybutyrate dehydrogenase, NAD and buffer. The second reagent R2 consist of surfactant, buffer, 4-nitrobenzene diazonium tetrafluroborate, ethylenediaminetetraacetic acid (sodium salt), sodium nitroferricyanide, yttrium and phosphoric acid trimorpholide. The reagents are placed on the autoanalyzer. The urine samples, standards and controls are placed in the autoanalyzer specimen cups. The urine samples, standards and controls are aliquoted into cuvettes and mixed with the first reagents The second reagent is added and mixed and the solution is read at specified intervals as dictated by the instrument parameters and at the specified wavelength (monochromatically) depending on reagent combination used. Analyzer temperature is set at 37 degrees C. In this instance, the assay is read at 645 nanometers and read times are specific to the analyzer. NOTE: the result of this assay is equivalent to 99% of total ketone bodies present in the test samples.

EXAMPLE 2

The automated total ketone bodies urinalysis reagent system's single reagent contains, ethylenediaminetetraacetic acid, NAD, Delta-3-hydroxybutyrate hydrogenase, buffers and surfactants. The reagents are placed on the autoanalyzer. The urine samples, standards and controls are placed in the autoanalyzer specimen cups. The urine samples, standards and controls are aliquoted into cuvettes, mixed with the first reagent, and the solution is read at specified intervals as dictated by the instrument parameters and at the specified wavelength (monochromatically) depending on reagent combination used. Analyzer temperature is set at 37 degrees C. In this instance, the assay is read at 340 nanometers and read times are specific to the analyzer. NOTE: the result must be multiplied by 1.25, because this method only measures 80% of the ketone bodies present (B-hydroxybutyric acid).

EXAMPLE 3

The automated total ketone bodies urinalysis reagent system's first reagent (R1) contains surfactants, buffer, NAD and ethylenediaminetetraacetic acid. The second reagent (R2) consists of buffer, Delta-3-hydroxybutyrate dehydrogenase and surfactants. The reagents are placed in the autoanalyzer. The urine samples, standards and controls are placed in the autoanalyzer specimen cups. The urine samples, standards and controls are aliquoted into cuvettes and mixed with the first reagent. The second reagent is added and mixed and the solution is read at specified intervals as dictated by the instrument parameters and at the specified wavelength (monochromatically) depending on reagent combination used. Analyzer temperature is set at 37 degrees C. In this instance, the assay is read at 340 nanometers and read times are specific to the analyzer. NOTE: the result must be multiplied by 1.25, because this method only measures 80% of the total ketone bodies present (B-hydroxybutyric acid).

EXAMPLE 4

The automated total ketone bodies urinalysis reagent system's first reagent (R1) contains surfactant, ethylenediaminetetraacetic acid (sodium salt), Delta-3-hydroxybutyrate dehydrogenase, glycine and buffer. The second reagent R2 consists of surfactant, buffer, sodium nitroferricyanide. The reagents are placed on the autoanalyzer. The urine samples, standards and controls are placed in the autoanalyzer specimen cups. The urine samples, standards and controls are aliquoted into cuvettes, mixed with the first reagent, the second reagent is added and mixed and the solution is read at specified intervals as dictated by the instrument parameters and at the specified wavelength (monochromatically) depending on reagent combination used. Analyzer temperature is set at 37 degrees C. In this instance, the assay is read at 545 nanometers and read times are specific to the analyzer. NOTE: the result of this assay is equivalent to 99% of total ketone bodies present in test samples.

EXAMPLE 5

The automated total ketone bodies urinalysis reagent system's first reagent (R1) contains surfactant, ethylenediaminetetraacetic acid (sodium salt), Delta-3-hydroxybutyrate dehydrogenase, glycine, NAD and buffer. The second reagent R2 consists of surfactant, buffer, sodium nitroferricyanide. The reagents are placed on the autoanalyzer. The urine samples, standards and controls are placed in the autoanalyzer specimen cups. The urine samples, standards and controls are aliquoted into cuvettes and mixed with the first reagent. The second reagent is added and mixed and the solution is read at specified intervals as dictated by the instrument parameters and at the specified wavelength (monochromatically) depending on reagent combination used. Analyzer temperature is set at 37 degrees C. In this example, the analyzer measures the absorbance after the addition of the first reagent at 340 nm, and calculates the amount of Beta-hydroxybutyric acid (BHBA). After the addition of the second reagent the analyzer again measures the absorbance, but this time at 540 nm, thereby determining the total amount (99%) of the ketone bodies present (i.e., BHBA, and acetoacetic acid, AAA). The analyzer is preprogramed to report this total, and the ratio of AAA to BHBA. This total and ratio are very important to the attending physician monitoring the progress of a diabetic patient. NOTE: the result of this assay is equivalent to 99% of total ketone bodies present in test samples.

We claim:

1. An automated method for detecting total ketone bodies in a patient's urine sample without employing an impregnated test strip, the steps comprising placing an aliquot of the urine to be tested in a first automated analyzer sampling cup, placing a standard containing a known concentration of total ketone bodies in a second automated analyzer sampling cup, placing the cups in a sampling tray within the automated analyzer, transferring the urine from the first sampling cup to a cuvette mounted within the automated analyzer, injecting at least one reagent composition in an aqueous medium into the cuvette, wherein said at least one reagent composition comprises a compound to remove substances in the urine interfering with colorimeter reaction selected from the group consisting of 2, 3-butanedione monoxime, ethylenediaminetetraacetic acid and dimercaptopropanol, and a compound to convert B-hydroxybutyric acid in the urine to acetoacetic acid in the presence of nicotinamide adenine dinucleotide, reading at specified intervals, in accordance with a preprogrammed code introduced into the automated analyzer, at a preprogrammed monochromatically specified wavelength, to compare absorbance of the patient's urine and reagent composition complex with that of the standard and thereby quantitatively determining the presence of total ketone bodies in the patient's urine.

2. The method according to claim 1 wherein there is a first and second reagent composition in an aqueous medium injected into the cuvette.

3. The method according to claim 1 wherein the wavelength of the analyzer is about 340 nanometers to 700 nanometers.

4. The method according to claim 1 wherein said at least one reagent composition further comprises a first reagent composition comprising a buffer to adjust the pH of the urine to a preferred value, a surfactant, the compound to remove substances in the urine that cause interference with calorimetric photometry, Delta-3-hydroxybutyrate dehydrogenase to convert the B-hydroxybutyric acid to acetoacetic acid and a second reagent composition comprising diazonium salt, a salt of ethylenediaminetetraacetic acid, and the wavelength of the analyzer is about 645 nm.

5. The method according to claim 4 wherein the diazonium salt is 4-nitrobenzene diazonium tetrafluoroborate and the salt of ethylenediaminetetraacetic acid is the sodium salt.

6. The method according to claim 1 wherein said at least one reagent composition further comprises a first reagent composition comprising a buffer to adjust the pH of the urine to a preferred value, a surfactant, the compound to remove substances in the urine that cause interference with calorimetric photometry, an amino acid, Delta-3-hydroxybutyrate dehydrogenase to convert the B-hydroxybutyric acid to acetoacetic acid and a second reagent composition comprising sodium nitroferricyanide, buffers, surfactant, and the wavelength of the analyzer is about 540 nm.

7. The method according to claim 6 wherein the amino acid is glycine and the compound to remove interfering substances from the urine is ethylenediaminetetraacetic acid sodium salt.

8. The method according to claim 6 wherein the first reagent composition also contains NAD or NADP to quantify total ketones.

* * * * *

UNITED STATES PATENT AND TRADEMARK OFFICE
CERTIFICATE OF CORRECTION

PATENT NO. : 5,801,059
DATED : September 1, 1998
INVENTOR(S) : Jack V. Smith et al.

It is certified that error appears in the above-identified patent and that said Letters Patent is hereby corrected as shown below:

Title page, Item [60],
Related U.S. application Data, please delete "continuation-in-part of Ser. No. 68,956" and insert -- continuation of Ser. No. 68,956 --.

Title page,
Abstract,
Line 7, please delete "calorimetric" and insert -- colorimetric --.

Column 1,
Line 8, please delete "continuation-in-part" and insert -- continuation --.

Column 5,
Line 54, please delete "calorimetric" and insert -- colorimetric --.

Column 10,
Lines 5-6, please delete "calorimetric" and insert -- colorimetric --.

Signed and Sealed this

Twenty-seventh Day of November, 2001

*Attest:*

NICHOLAS P. GODICI
*Attesting Officer* — Acting Director of the United States Patent and Trademark Office